US012758792B2

(12) United States Patent
Plewa

(10) Patent No.: US 12,758,792 B2
(45) Date of Patent: Oct. 13, 2026

(54) METHOD FOR ESTIMATING A TOTAL SCATTER FACTOR IN DOSE CALCULATION FOR RADIOTHERAPY

(71) Applicant: Brainlab AG, Munich (DE)

(72) Inventor: Philipp Plewa, Munich (DE)

(73) Assignee: Brainlab SE, Munich (DE)

( * ) Notice: Subject to any disclaimer, the term of this patent is extended or adjusted under 35 U.S.C. 154(b) by 319 days.

(21) Appl. No.: 17/766,580

(22) PCT Filed: Mar. 30, 2021

(86) PCT No.: PCT/EP2021/058355

§ 371 (c)(1),
(2) Date: Apr. 5, 2022

(87) PCT Pub. No.: WO2022/207085

PCT Pub. Date: Oct. 6, 2022

(65) Prior Publication Data

US 2024/0100359 A1 Mar. 28, 2024

(51) Int. Cl.
*A61N 5/10* (2006.01)

(52) U.S. Cl.
CPC ........... *A61N 5/103* (2013.01); *A61N 5/1031* (2013.01); *A61N 5/1047* (2013.01); *A61N 5/1075* (2013.01)

(58) Field of Classification Search
CPC .... A61N 5/103; A61N 5/1031; A61N 5/1047; A61N 5/1075; A61N 5/1045
See application file for complete search history.

(56) References Cited

U.S. PATENT DOCUMENTS 5,778,043 A * 7/1998 Cosman ............... A61N 5/1049 378/65
2006/0203964 A1 * 9/2006 Nyholm ............... A61N 5/1031 378/65

OTHER PUBLICATIONS

McDonough, J., Xiao, Y., & Bjamgard, B. E. (1999). Comparing two methods for calculating Phantom Scatter. Physics in Medicine and Biology, 44(2). https://doi.org/10.1088/0031-9155/44/2/023 (Year: 1999).*

(Continued)

*Primary Examiner* — Charles A Marmor, II
*Assistant Examiner* — Marc D. Honrath
(74) *Attorney, Agent, or Firm* — Tucker Ellis LLP

(57) ABSTRACT

Provided is a method for estimating a total scatter factor in dose calculation for radiotherapy, wherein a linear accelerator, LINAC, is used to irradiate a medium. This method includes receiving geometric data of the LINAC, wherein the geometric data comprises geometric information about collimating devices of a LINAC head of the LINAC. The method further includes determining a head scatter factor based on a geometric head model using the received geometric data, wherein the head scatter factor quantifies a scatter contribution from the LINAC head, and determining a phantom scatter factor based on an empiric phantom scatter formula using the received geometric data, wherein the phantom scatter factor quantifies a scatter contribution from the irradiated medium. The method provides for determining an estimated total scatter factor using the determined head scatter factor and the determined phantom scatter factor.

19 Claims, 4 Drawing Sheets

(56) References Cited

OTHER PUBLICATIONS

Shih, R., Li, X. A., Chu, J. C., & Hsu, W.-L. (1999). Calculation of head scatter factors at Isocenter or at center of field for any arbitrary jaw setting. Medical Physics, 26(4), 506-511. https://doi.org/10.1118/1.598549 (Year: 1999).*
Tahmasebi Birgani, M. J., Chegeni, N., & Behrooz, M. A. (2017). An analytical method to calculate phantom scatter factor for photon beam accelerators. Electronic Physician, 9(1), 3523-3528. https://doi.org/10.19082/3523 (Year: 2017).*
International Search Report, corresponding to application serial No. PCT/EP2021/058355, filed Mar. 30, 2021, 14 pages.
Lorenz, Friedlieb, et al. An Independent dose calculation algorithm for MLC-based stereotactic radiotherapy, Apr. 19, 2007, 10 pages.
Zhu, Timothy C., et al. Report of AAPM Therapy Physics Committee Task Group 74: In-air output ratio, S?, for megavoltage photon beams, Oct. 20, 2009, 32 pages.
Lorenz, Friedlieb, et al. An independent dose calculation algorithm for MLC-based radiotherapy including the spatial dependence of MLC transmission, Jan. 7, 2008, 18 pages.
Georg, Dietmar, et al. On empirical methods to determine scatter factors for irregular MLC shaped beams, Jul. 14, 2004, 8 pages.
Alaei, Parham et al. Effect of multileaf collimator-defined segment size on S?, May 19, 2010, 8 pages.

* cited by examiner

METHOD FOR ESTIMATING A TOTAL SCATTER FACTOR IN DOSE CALCULATION FOR RADIOTHERAPY

RELATED APPLICATION DATA

This application is a national phase application of International Application No. PCT/EP2021/058355, filed Mar. 30, 2021, the contents of which are incorporated herein by reference.

FIELD OF THE INVENTION

The present invention relates to a computer-implemented method for estimating a total scatter factor in dose calculation for radiotherapy, a corresponding radiotherapy treatment system, a corresponding use of the method for a pencil beam algorithm based dose calculation, a corresponding computer program and a method for commissioning a linear accelerator.

TECHNICAL BACKGROUND

In radiotherapy, a linear accelerator, LINAC, is used for treating a biological targets like brain metastases or other tumors by irradiation with ionizing radiation. It is important that the dose actually delivered by the LINAC to the patient matches the planned dose. Therefore, a LINAC has to be calibrated before it can be used for patient treatment, and dose algorithms are used to estimate the dose applied to the targets for treatment planning. Those dose algorithms inter alia determine the intensity of the irradiation delivered by the LINAC to the targets. For a specific irradiated field, this is indicated by a so called scatter factor or output factor.

A typical pencilbeam dose algorithm might determine total scatter factors by linear interpolation in a two-dimensional table, which contains scatter factors measured in advance, when calibrating the machine, for different combinations of simplified multi leaf collimator, MLC, and jaw configurations, for example a number of square fields. To determine scatter factors for arbitrary MLC shapes—considering, for example, multiple openings or jaw clipping (e.g. some field edges in the beam's eye view being collimated by the jaws), or very small field sizes—the algorithm may resort to empirical weighting factors and logarithmic extrapolation.

For complex treatment plans, which can include MLC shapes composed of multiple openings with different sizes, some of which may be very small or partially clipped by the jaws, significant deviations between planned and delivered dose can occur as a result of the approximations intrinsic to a table-based scatter factor calculation.

The present invention has the object of providing an improved method for estimating a scatter factor in dose calculation for radiotherapy, in particular for complex treatment plans.

The present invention can be used for radiotherapy treatment planning e.g. in connection with a system such as the Brainlab Elements, products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

A computer-implemented method for estimating a total scatter factor in dose calculation for radiotherapy, wherein a linear accelerator, LINAC, is used to irradiate a medium is presented.

In particular, in this method geometric data of the LINAC is received, wherein the geometric data comprises geometric information about collimating devices of a LINAC head of the LINAC. A head scatter factor is determined based on a geometric head model using the received geometric data, wherein the head scatter factor quantifies a scatter contribution from the LINAC head. A phantom scatter factor is determined based on an empiric phantom scatter formula using the received geometric data, wherein the phantom scatter factor quantifies a scatter contribution from the irradiated medium. An estimated total scatter factor is determined using the determined head scatter factor and the determined phantom scatter factor. Thus, the proposed method inter alia allows to improve a dose calculation accuracy for complex radiotherapy treatment, in particular including small or multiple opening of the multi leaf collimator.

GENERAL DESCRIPTION OF THE INVENTION

In this section, a description of the general features of the present invention is given for example by referring to possible embodiments of the invention.

According to an aspect of the present disclosure, a computer-implemented method for estimating a total scatter factor in dose calculation for radiotherapy, wherein a linear accelerator, LINAC, is used to irradiate a medium, comprises the following steps: In a first step, geometric data of the LINAC is received, wherein the geometric data comprises geometric information about a LINAC head of the LINAC, wherein the LINAC head comprises at least one collimating device and at least one irradiation source. In another step, a head scatter factor is determined based on a geometric head model using the received geometric data, wherein the head scatter factor quantifies a scatter contribution from the LINAC head. In another step, a phantom scatter factor is determined based on an empiric phantom scatter formula using the received geometric data, wherein the phantom scatter factor quantifies a scatter contribution from the irradiated medium. In another step, an estimated total scatter factor is determined using the determined head scatter factor and the determined phantom scatter factor.

In radiotherapy, in general, a LINAC is used for irradiating a medium, which is also referred to as target, in particular an organic target. The irradiation dose that the LINAC applies to the medium should be as high as necessary to achieve the effect of radiotherapy, but as low as possible so that the irradiation exposure to the medium does not exceed a critical irradiation dose. For example, the irradiation dose of the LINAC should be high enough to damage a tumour of a patient, but as low as possible to minimize the negative effects of irradiation to the patient. In general, an irradiation beam of the LINAC is restricted, or in other words formed, by at least one collimating device that is disposed between the LINAC and the irradiated medium.

The term "total scatter factor", which is also referred to as relative output factor, is used in radiotherapy to provide information of a relevant output of a LINAC relative to the nominal output of the LINAC. In other words, the total scatter factor is defined as a ratio of a measured irradiation dose of the LINAC on a reference field and a distributed irradiation dose of the LINAC. The total scatter factor comprises two components, a head scatter factor and a phantom scatter factor. Preferably, the total scatter factor is defined by the product of head scatter factor and phantom scatter factor.

The term "head scatter factor", as used herein, is also referred to as collimator scatter factor. The head scatter factor indicates a contribution to the irradiation dose of the LINAC related to production and shaping of the irradiation beam of the LINAC.

The term "phantom scatter factor", as used herein, indicates a contribution to the irradiation dose of the LINAC by the phantom itself. The phantom, which is also referred to as test phantom, is a test subject used for reference measurement of a irradiation dose of the LINAC. In other words, the irradiation of the LINAC is applied to the phantom instead of a tissue of a patient. For example, the phantom comprises a tank full of liquid to simulate the tissue of the patient.

Preferably, the geometric data is extracted from a treatment plan. The treatment plant comprises LINAC specification data, wherein the LINAC specification data comprises information about the LINAC, in particular the geometric information. The LINAC specification data preferably comprises information like a material type of the MLC, a material type of the jaws, a shape of the leaves of the MLC, a shape of the jaws and an optic type of the LINAC.

Preferably, the geometric head model comprises geometric data of the LINAC head, reflecting a spatial arrangement of the different components of the LINAC head, in particular the at least one collimating device, the at least one irradiation source and/or the at least one jaw. Further preferably, the geometric head model comprises at least one geometric parameter that is used to reflect a geometry and calibration of the LINAC. Thus, for each particular geometry and calibration of each LINAC, an improved accuracy of scatter factor determination, in particular for small LINAC openings, is provided.

Preferably, the head scatter factor is normalized before being multiplied with the head scatter factor.

Preferably, the total scatter factor is directly used in the dose algorithm, in particular the pencilbeam dose algorithm. Thus, a two-component model is provided focusing on the head scatter factors and the phantom scatter factors.

Using geometric data of the LINAC head together with a geometric head model for the head scatter and an empiric formula for the phantom scatter allows for an improved accuracy in estimating the total scatter factor. Consequently, the accuracy of dose calculation, in particular using a pencilbeam dose algorithm, is improved.

Using the geometric head model to determine the head scatter factor and the empiric phantom scatter formula to determine the phantom scatter factor allows providing a physics based model for estimating the total scatter factor. Thus, dose calculation accuracy for complex radiotherapy treatment plans, in particular including small or multiple openings, further in particular of a MLC, is improved. This is especially helpful, when planning non-isocentric treatments of multiple brain metastases.

Preferably, a complex radiotherapy plan preferably comprises a collimator device with multiple openings of different sizes, some of which may be very small or partially clipped, in particular by jaws.

Thus, an improved computer-implemented method for estimating a total scatter factor in dose calculation for radiotherapy is provided.

According to another exemplary embodiment of the present invention, the collimating device comprises at least one multi leaf collimator, MLC, defining an MLC plane perpendicular to a irradiation direction of the LINAC, and jaws defining a jaw plane perpendicular to the irradiation direction of the LINAC. The geometric data of the LINAC comprises leaf positions of leaves of the MLC and a jaw position of the jaws.

The method comprises the following steps. In a step, at least one MLC opening in the MLC is determined using the received leaf positions. In another step, for each MLC opening, a rectangular equivalent field is determined using the received leaf positions. In another step, for each MLC opening, the head scatter factor is determined based on the geometric head model using the determined rectangular equivalent field and the jaw position. In another step, for each MLC opening, phantom scatter factor is determined based on the empiric formula using the determined rectangular equivalent field and the jaw position.

The term "rectangular equivalent field", as used herein, comprises an area defined at an MLC opening that is used as an equivalent approximation of the MLC opening for further processing in head scatter factor and phantom scatter factor calculation. The MLC opening is also referred to as MLC field.

Preferably, determining the phantom scatter factor comprises determining a scatter-to-primary ratio, SPR, which depends primarily on the size of the rectangular equivalent, in particular of the effective field. In addition a lack of electronic equilibrium for small fields is taken into account as well.

The SPR is defined according to formula 1:

$$SPR = b\frac{sd}{cs + d} \tag{1}$$

wherein s is the equivalent field size, d is a calibration depth, defining how deep a reference target for calibration is within the phantom, and b, c are tuneable parameters.

The proportionality of the phantom scatter factor is thus defined by formula 2:

$$Sp \propto \left(1 - ae^{-\frac{s}{l}}\right)(1 + SPR) \tag{2}$$

wherein a, l are tuneable parameters.

The multi leaf collimator preferably comprises a plurality of movable leaves. The leaves are further preferably moveable in a direction perpendicular to the irradiation direction of the LINAC. Further, the leaves of the multi leaf collimator preferably for pairwise lines of leaves. This allows disposing the leaves in such a way in the MLC plane that at least one MLC opening is determined. The shape and/or dimension of the MLC opening can thus be adjusted by moving one or more leaves in the MLC plane. In other words, the shape and/or dimension of the MLC opening can be derived from leaf positions of the MLC leaves.

Due to the leaves of the multi leaf collimator, the at least one MLC opening in general has an irregular shape. The rectangular equivalent field defines a regular approximation of the at least one MLC opening. In other words, for each MLC opening, a rectangular equivalent field is defined. Due to the regularity of the rectangular equivalent field, an improved input for the determination of the phantom scatter factor is provided. This allows the usage of a less complex empiric formula for determining the phantom scatter factor.

Preferably, the leaves have a longitudinal rectangular shape. The leaves preferably comprise a height of 2.5 mm. Further preferably, the leaves comprise a height of 5 mm. The term "height", as used in this context, describes a dimension of the leaf in the MLC plane in a height direction, perpendicular to a length direction of the leaf in the MLC plane. In other words, the height of the leaf is defined as a dimension of the leaf both perpendicular to the direction of leaf movement and perpendicular to the irradiation beam.

It should also be noted that the application of leaf collimators in the field of radiotherapy are well known by the skilled person and it is exemplarily referred here to Brainlab AG's patent application WO 2013/075743 where its described in the context of FIGS. 3 and 4 how the leaves can be adjusted to target the target volume, i.e. one or more metastases.

Preferably, the jaw plane is disposed between the irradiation source and the MLC plane. However, the MLC plane can also be disposed between the irradiation source and the MLC plane.

Preferably, a determination of the rectangular equivalent field for each of the MLC opening uses the leaf positions of the MLC leaves as input. For each MLC opening, the rectangular equivalent field is determined based on the leaf positions, resulting in a set of rectangular equivalent fields corresponding to the MLC openings.

Thus, an improved computer-implemented method for estimating a total scatter factor in dose calculation for radiotherapy is provided.

According to another exemplary embodiment of the present invention, determining the rectangular equivalent field comprises determining a bounding box around the opening of the MLC plane and determining the rectangular equivalent field by scaling down the bounding box that the scaled down bounding box covers an area equal to the MLC opening.

Preferably, scaling down comprises a reduction of dimension of the bounding box, wherein a ratio of width and height of the bounding box remains constant.

In other words, the bounding box is determined using an extension of the MLC opening in each direction taking into account a possible clipping of the MLC opening by the jaw. Consequently, unless the MLC opening is rectangular in the first place, the bounding box covers a rectangular area that is larger than the MLC opening. Therefore, the bounding box is scaled down, keeping the shape of the bounding box, until the area that is covered by the bounding box is equivalent to the area that the MLC opening covers.

Thus, an improved computer-implemented method for estimating a total scatter factor in dose calculation for radiotherapy is provided.

According to another exemplary embodiment of the present invention, determining the rectangular equivalent field comprises determining a radiologic field using the received leaf positions, wherein the radiologic field reflects a geometric design of the leaves of the MLC, and determining the rectangular equivalent field using the radiologic field.

In particular at the edges of the MLC, additional physical effects in regard of the irradiation beam of the LINAC occur. In other words, there are uncertainties at the edges of the MLC that do not allow considering the edges of the leaves as sharp edges. In order to represent those physical effects, before determining the rectangular equivalent field, using the determined leaf positions a radiologic field is determined. The radiologic field differs from the MLC field defined by the geometry of the MLC opening in both directions of the MLC plane. In particular, the directions in the MLC plane comprise an x-direction in a length direction of the MLC leaves, and an y-direction in a height direction of the MLC leaves. The field difference in the y-direction depends mainly on the geometric design of the leaf and thus is independent of MLC modifications. Modifications of the MLC in the x-direction might lead to a slightly different radiologic field.

Using the radiologic field as the basis for the determination of the rectangular equivalent field allows for providing an improved-computer implemented method for estimating a total scatter factor in dose calculation for radiotherapy.

According to another exemplary embodiment of the present invention, determining the head scatter factor comprises for each rectangular equivalent field the following steps. In one step, the MLC plane is shifted so that a centre of the rectangular equivalent field is disposed on a central axis of the LINAC along the irradiation direction of the LINAC. In another step, the jaw plane is shifted by the same amount as the MLC plane so that a spatial alignment of the jaws to the MLC openings does not change. In another step, a detector eye view is determined, being a part of a LINAC source plane that is visible from a detector position, wherein the irradiation source of the LINAC is disposed in the LINAC source plane wherein the detector position is defined by an intersection of the central axis of the LINAC and a detector plane on which the irradiation of the LINAC is detected. In another step, the head scatter factor is determined by determining a total intensity of the irradiation source in the detector's eye view. In particular, the source may only be partially visible.

By shifting the jaw plane and the MLC plane in the same manner, it is assured that any clipping of a jaw of the rectangular equivalent field is not distorted by the shifting.

The detector eye view indicates the part of the irradiation source that is visible by the target through the collimator devices.

The size of the irradiation source, in particular a relevant part of the irradiation source in view of the MLC openings, is an important factor for calculating an irradiation dose provided by the LINAC to the respective targets.

The shifting step allows providing an accurate representation of the irradiation relevant part of the irradiation source for each MLC opening, taking into account the lateral restrictions of the irradiation beam by the collimator devices. Thus, for each irradiation beam through each MLC opening, scatter factors can be determined.

Thus, an improved computer-implemented method for estimating a total scatter factor in dose calculation for radiotherapy is provided.

According to another exemplary embodiment of the present invention, the irradiation source comprises at least one Gaussian source, approximating of the irradiation source.

Thus, the actual irradiation source is approximated by the at least one Gaussian source.

According to another exemplary embodiment of the present invention, the irradiation source comprises a plurality of Gaussian sources at different heights in the LINAC head, approximating of the irradiation source.

Depending on the different effects, like the influence of a flattening filter or irradiation scatter at the jaws of the LINAC, the different irradiation sources should reflect, the irradiation sources are disposed at different heights in the LINAC head.

According to another exemplary embodiment of the present invention, the plurality of Gaussian sources comprises a primary source and at least one secondary source.

Preferably, the LINAC source comprises a first secondary source reflecting a flattening filter of the LINAC and a second secondary source reflecting a scatter of the irradiation at the jaws of the LINAC.

According to another exemplary embodiment of the present invention, the head model further comprises adjustable fit head parameters and fixed head parameters, depending on a configuration of the LINAC and a measurement setup of the LINAC.

Preferably, the fit head parameters are tuneable, in particular during calibration of the LINAC. Further preferably, the fixed head parameters are set by the configuration of the LINAC and/or the measurement setup in which the LINAC is used.

Thus, the head model provides a flexible calculation basis that can be adapted to different LINAC designs and measurement setups.

According to another exemplary embodiment of the present invention, the fit head parameters comprise a dimension of the primary source and/or a dimension and weight relative to the primary source of the at least one secondary source.

According to another exemplary embodiment of the present invention, the fixed head parameters comprise a distance of the secondary sources from the primary source, a distance of the jaw plane from the primary source, a distance of the MLC plane from the primary source, a source-surface distance, being a distance between the irradiation source and a surface plane to be irradiated by the LINAC, and/or a measurement depth, being distance between the surface plane to be irradiated by the LINAC and the detector position.

According to another exemplary embodiment of the present invention, the phantom scatter formula comprises adjustable fit phantom parameters and fixed phantom parameters, depending on a configuration of the LINAC and/or a measurement setup of the LINAC.

Preferably, the fit phantom parameters are tuneable, in particular during calibration of the LINAC. Further preferably, the fixed phantom parameters are set by the configuration of the LINAC and/or the measurement setup in which the LINAC is used.

Thus, the head model provides a flexible calculation basis that can be adapted to different LINAC designs and measurement setups.

According to another exemplary embodiment of the present invention, the fixed phantom parameters comprise the rectangular equivalent field and/or a measurement depth.

The measurement depth, which is also referred to as calibration depth, relates to a depth of a reference target for irradiation within the phantom. In other words, the measurement depth is defined by a distance between a surface plane, defined by the surface of the phantom to be irradiated, and a detector plane, defined by the position of the reference target to be irradiated.

According to another exemplary embodiment of the present invention, the MLC leaf positions comprise two leaf coordinates for every each pair of leaves of the MLC.

Preferably, each pair of leaves comprises a left leaf and a right leaf, wherein each leaf coordinate reflects a position of the left leaf and a position of the right leaf. An MLC opening occurs when there is a distance between a right end of the left leaf and a left end of the right leaf.

Further technical details on coordinates, movements and scales of the MLC are standardized in IEC-1217.

According to another exemplary embodiment of the present invention, the jaw plane comprises four jaws and wherein the jaw position comprises one coordinate for each jaw.

Preferably, the LINAC comprises four jaws, which restrict the irradiation of the LINAC in each direction lateral to the irradiation direction. The jaws are in general referred to as X1, X2, Y1 and Y2. Consequently, the jaw position comprises an X1-coordinate, an X2-coordinate, an Y1-coordinate and an Y2-coordinate.

According to another exemplary embodiment of the present invention, the at least one MLC opening is smaller than 5 cm in one direction.

Preferably, an MLC opening is considered as a small MLC opening, when shadowing effects become especially relevant in the scatter factor calculation. This is the case, if the MLC opening is smaller than 5 cm in one direction.

According to another aspect of the present invention, a method for commissioning a linear accelerator, LINAC, comprises the following steps. In one step, the total scatter factor of the LINAC is measured by using a measurement setup. In another step, using the measured total scatter factor, the geometric head model and the empiric phantom scatter formula is automatically optimized by using the method for estimating a total scatter factor in dose calculation for radiotherapy, as described herein.

In other words, the adjustable parameters of the geometric head model and the empiric phantom scatter formula, in particular the fit head parameter and the fit phantom parameter, are tuned by comparing the estimated total scatter factor with the measured total scatter factor.

Preferably, a customer measures total scatter factors for a sufficient number of square or rectangular MLC and jaw fields. The parameters of the scatter model, in particular the geometric head model, the empiric phantom scatter formula and a model for determining the total scatter factors, are automatically optimized based on the measured scatter factors. Further preferably, the customer verifies the best-fit results by comparing the scatter factors predicted by the model to the measured values. This comparison can also be done automatically by the scatter model itself. If the measured values and the determined total scatter factor deviate in such a way that they exceed a predetermined threshold, a warning is issued.

Preferably, the geometric head model and the empiric phantom formula are designed in a way that a risk of using un-physical scatter values, or in other words an un-physical total scatter factor, in the dose calculation is minimized. This is in particular achieved by the general structure of the geometric head model and the empiric phantom formula containing fit and fix parameters.

According to another exemplary embodiment of the present invention, the method comprises the step of determining a deviation between a best-fit result of the estimated total scatter factor and the measured total scatter factor, and when the deviation exceeds a threshold, provide a warning to a user.

According to another aspect of the present invention, a radiotherapy treatment system, being configured for executing the method for estimating a total scatter factor in dose calculation for radiotherapy, comprises the following. An input interface, configured for receiving geometric data of the LINAC, wherein the geometric data comprises geometric information about collimating devices of a LINAC head of the LINAC. A head scatter factor unit, configured for determining a head scatter factor based on a geometric head model using the received geometric data. A phantom scatter factor unit, configured for determining a phantom scatter factor based on an empiric phantom scatter formula using the received geometric data. A total scatter factor unit, configured for determining an estimated total scatter factor using the determined head scatter factor and the determined phantom scatter factor.

Preferably, the head scatter factor unit, the phantom scatter factor unit and the total scatter factor unit are referred to as scatter model. Based on input data, comprising the geometric data of the LINAC, the scatter model provides an estimated total scatter factor.

Thus, during commissioning of the LINAC, the scatter model is optimized by tuning adjustable parameters of the scatter model by comparing the estimated total scatter factor provided by the scatter model with a measured total scatter factor from a measurement setup.

Thus, the provided system comprises a scatter model that allows for an improved determination of an estimated total scatter factor in dose calculation for radiotherapy.

According to another aspect of the present invention, the method for estimating a total scatter factor in dose calculation for radiotherapy, as described herein, is used for a pencil beam algorithm based dose calculation.

According to another aspect of the present invention, a computer program which, when running on a computer or when loaded onto a computer, causes the computer to perform the method steps of the method for estimating a total scatter factor in dose calculation for radiotherapy, as described herein, and/or a program storage medium on which the program is stored, and/or a computer comprising at least one processor and a memory and/or the program storage medium, wherein the program is running on the computer or loaded into the memory of the computer, and/or a signal wave or a digital signal wave, carrying information which represents the program, and/or a data stream which is representative of the program.

For example, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Treatment Beam

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as irradiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising irradiation is for example used for the purpose of treatment. For example, the treatment beam comprises or consists of ionising irradiation. The ionising irradiation comprises or consists of particles (for example, sub-atomic particles or ions) or electromagnetic waves which are energetic enough to detach electrons from atoms or molecules and so ionise them. Examples of such ionising irradiation include x-rays, high-energy particles (high-energy particle beams) and/or ionising irradiation emitted from a radioactive element. The treatment irradiation, for example the treatment beam, is for example used in irradiation therapy or radiotherapy, such as in the field of oncology. For treating cancer in particular, parts of the body comprising a pathological structure or tissue such as a tumour are treated using ionising irradiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

Arrangement of Treatment Beams

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

BRIEF DESCRIPTION OF THE DRAWINGS

In the following, the invention is described with reference to the appended figures, which give background explanations and represent specific embodiments of the invention. The scope of the invention is however not limited to the specific features disclosed in the context of the figures, wherein FIG. 1 schematically shows a lateral view onto a LINAC for radiotherapy.

DESCRIPTION OF EMBODIMENTS

Figure 1:
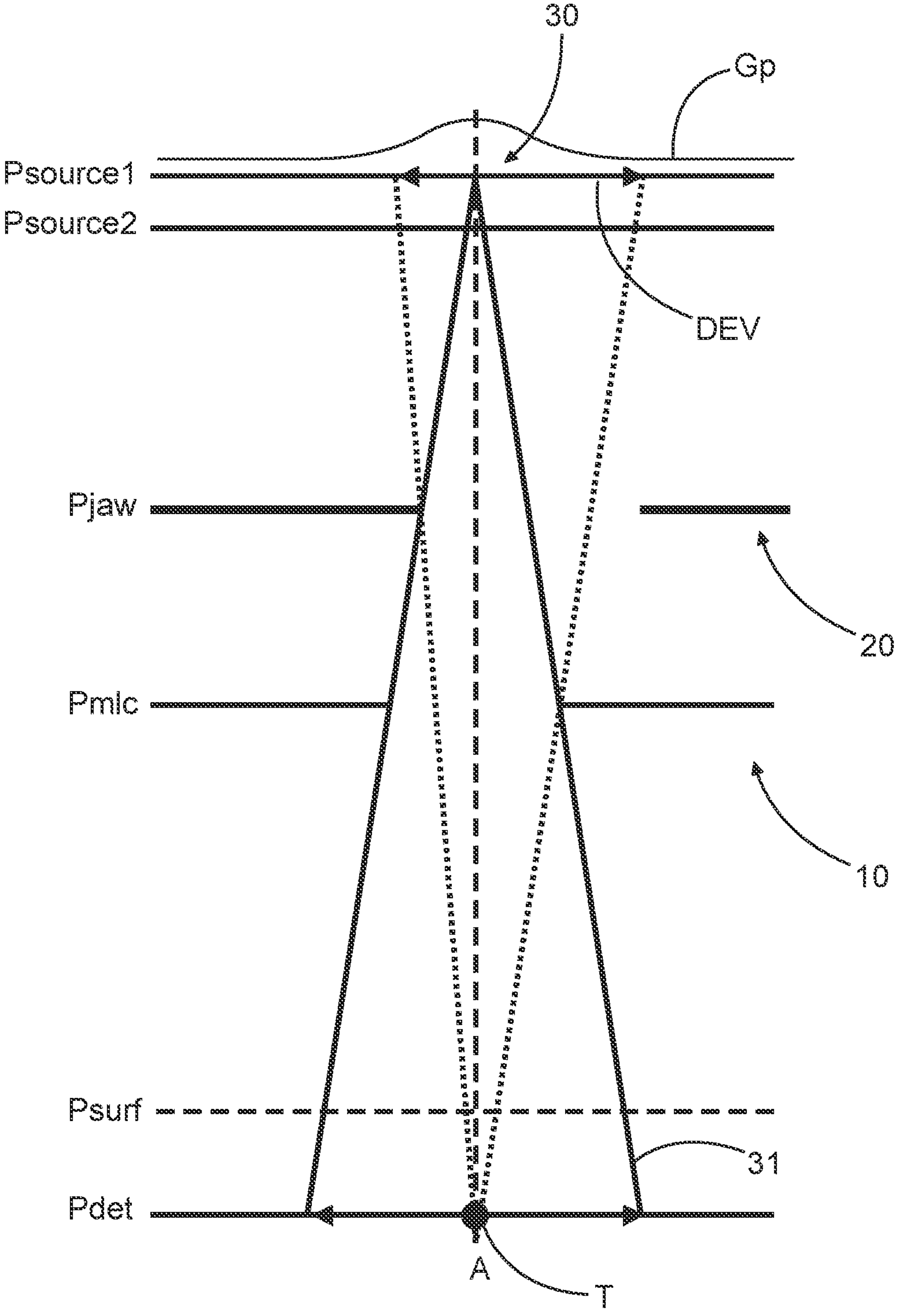

FIG. 1 schematically shows a lateral view onto a LINAC for radiotherapy. The LINAC comprises a LINAC head, wherein the LINAC head comprises an irradiation source 30, jaws 20 and a multi leaf collimator, MLC, 10. The irradiation source 30 is configured for providing an irradiation beam 31 that is used for irradiating a target T. In a calibration setup, the target T is a detection target T. The detection target is configured for detecting an irradiation dose provided by the LINAC. In a treatment setup, the target T is an organic target T, like brain metastasis, that are treated by irradiation from the LINAC.

The irradiation source 30 is approximated by a primary Gaussian source Gp and a secondary source (not shown). The primary Gaussian source Gp is disposed in a first source plane Psource1. The secondary source is disposed in a second source plane Psource2, wherein the second source plane Psource2 is disposed at a lower height as the first source plane Psource1. The terms lower and higher in view of the height of a plane is in this case seen from the primary Gaussian source Gp, which is the highest point of the arrangement, while the target T, being disposed in a detection plane Pdet, is the lowest point of the arrangement.

The jaws 20 are disposed in a jaw plane Pjaw, which itself is disposed between the first source plane Psource1 and the detection plane Pdet. The multi leaf collimator 10 is disposed in a MLC plane Pmlc, which itself is disposed between the first source plane Psource1 and the detection plane Pdet. In this case, the jaws 20 are disposed higher than the MLC 10. The jaws 20 and the multi loaf collimator 10 are collimator devices that are configured for laterally restricting the irradiation beam 31 from its way from the LINAC to the target T. The jaws 20 form a jaw opening in the jaw plane Pjaw through which the irradiation beam 31 can pass through. Thus, the jaws 20 laterally restrict the irradiation beam 31. The MLC 10 is configured for providing at least one MLC opening in the MLC plane, through which the irradiation beam 31 can pass through. Thus, the irradiation beam 31 of the LINAC is laterally restricted by the jaws 20 and the MLC 10.

The target T is usually not in air, but within a medium. In case of the calibration setup, the detection target T is within a phantom, which is preferably filled with liquid. The surface of the phantom thus defines a surface plane Psurf, disposed between the first source plane Psource1 and the detection plane Pdet. In case if the treatment setup, the organic target T is disposed within tissue of the patient to be treated. The skin of the patient thus defines the surface plane Psurf.

A detector eye view, DEV, represents the part of the first source plane Psource1 that is viewed from the target T through the MLC plane Pmlc and the jaw plane Pjaw onto the first source plane Psource1, as indicated with the dotted line.

In a case, wherein there are a plurality of MLC openings in the MLC, in a method for estimating a total scatter factor St in dose calculation for radiotherapy, as described herein, a head scatter factor is determined for each of the plurality of MLC openings.

The MLC plane Pmlc and the jaw plane Pjaw are shifted in a direction perpendicular to the irradiation beam 31 so that a centre of the MLC openings, or in particular a centre of a rectangular equivalent field F1, F2, F3 representing the MLC opening, is disposed on a central axis A of the LINAC along the irradiation direction of the LINAC.

Figure 2:
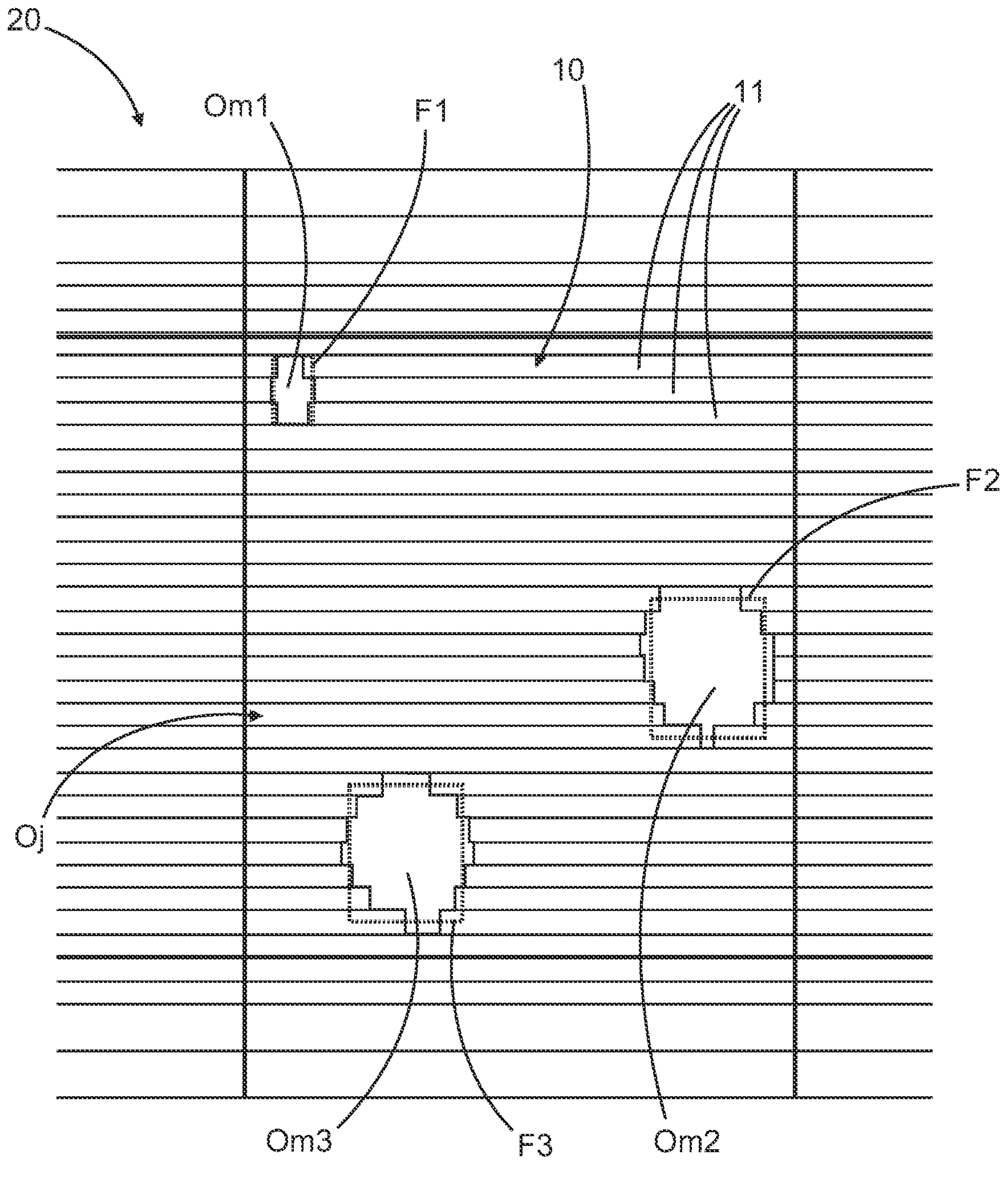
FIG. 2 illustrated a schematic view through the jaw plane and the MLC plane.

FIG. 2 illustrates a schematic view through the jaw plane and the MLC plane. It is shown that the jaw opening Oj of the jaws 20 provide a rough lateral restriction of the irradiation beam 31. Furthermore, it is shown that the MLC 10 comprises a first MLC opening Om1, a second MLC opening Om2 and a third MLC opening Om3 that are defined by the positions of the leaves 11 of the MLC 10. Each MLC opening Om1, Om2, Om3 covers a target to be irradiated by the LINAC. Thus, while the jaws 20 provide a rough lateral restriction of the irradiation beam 31, the MLC 10 provides a finer lateral restriction of the irradiation beam 31.

In a method for estimating a total scatter factor St in dose calculation for radiotherapy, as described herein, for each MLC opening Om1, Om2, Om3, a rectangular equivalent field F1, F2, F3 is determined based on the position of the leaves 11. In other words, a first rectangular equivalent field F1 is determined to approximate the first MLC opening Om1, a second rectangular equivalent field F2 is determined to approximate the second MLC opening Om2 and a third rectangular equivalent field F3 is determined to approximate the third MLC opening Om3. In the method for estimating a total scatter factor St in dose calculation for radiotherapy, the head scatter factor Sh and the phantom scatter factor are both determined using the respective rectangular equivalent fields F1, F2, F3 instead of the MLC openings Om1, Om2, Om3.

Figure 3:
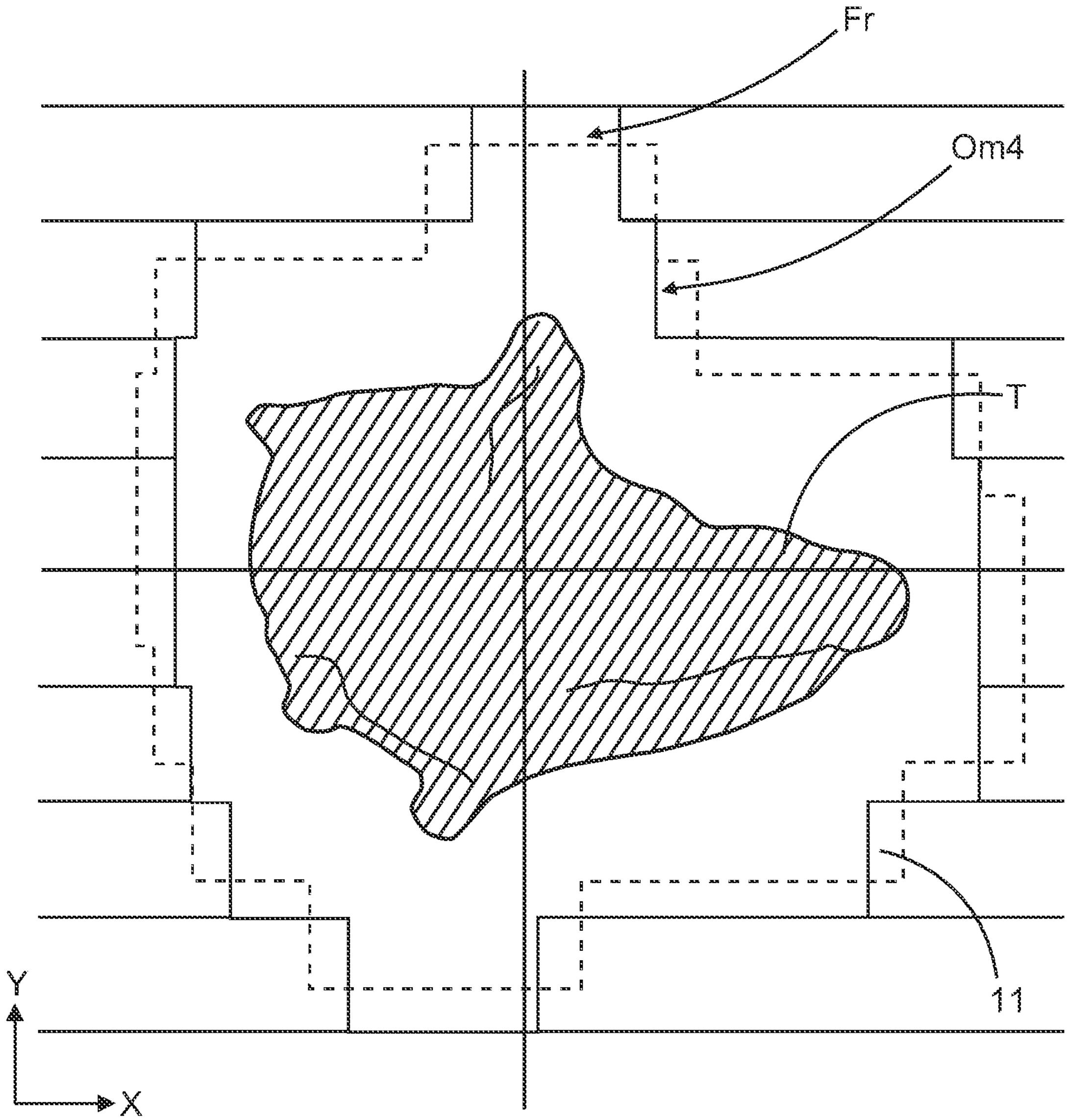
FIG. 3 schematically illustrates the difference between a geometric field and a medical field of an MLC opening.

FIG. 3 schematically illustrates the difference between a radiologic field Fr and a fourth MLC opening Om4. In reality, there are irradiating effects at the inner edges of the MLC leaves 11. Those irradiating effects comprise an uncertainty of blocking the irradiation beam 31 at the inner edges of the MLC leaves 11. Consequently, using the determined geometric fourth MLC opening Om4 based on the leave positions, a radiologic field Fr is determined taking into account that uncertainties. The radiologic field Fr differs from the geometric fourth MLC opening Om4 in both x- and y-direction. The field difference in a y-direction, in particular tongue and groove size of the MLC leaves, depends mainly on the geometric design of the MLC leaves and thus is independent of MLC modifications. Modifications to the MLC in an x-direction might lead to slightly different radiologic field corrections.

Figure 4:
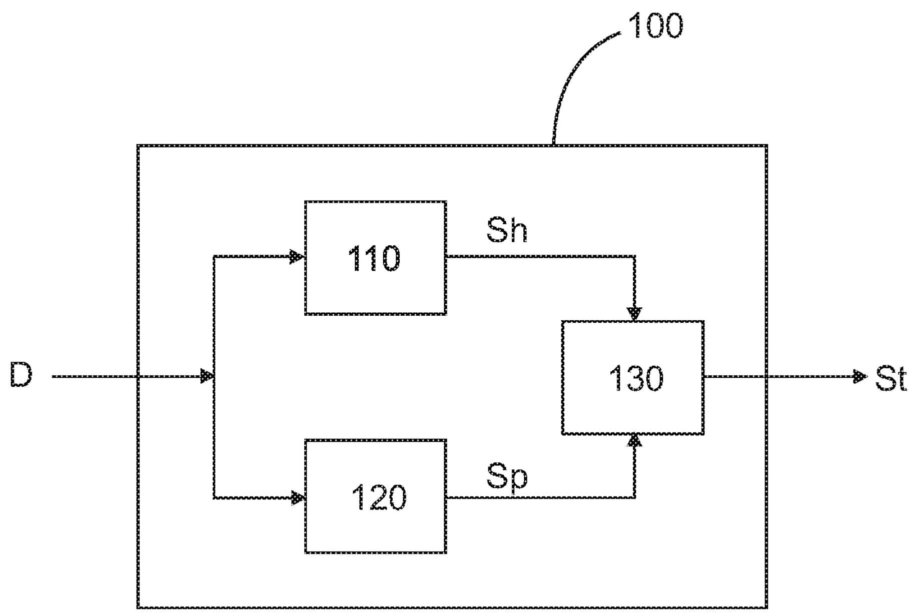
FIG. 4 schematically illustrates a radiotherapy treatment system.

FIG. 4 schematically illustrates a radiotherapy treatment system 100. The radiotherapy treatment system 100 is configured for executing the method for estimating a total scatter factor St in dose calculation for radiotherapy, as described herein. The radiotherapy treatment system 100 is configured for receiving geometric data D of the LINAC, in particular via an input interface, wherein the geometric data D comprises geometric information about collimating devices 10, 20 of a LINAC head of the LINAC. The radiotherapy treatment system 100 comprises a head scatter factor unit 110, configured for determining a head scatter factor Sh based on a geometric head model using the received geometric data D. Further, the radiotherapy treatment system 100 comprises a phantom scatter factor unit 120, configured for determining a phantom scatter factor Sp based on an empiric phantom scatter formula using the received geometric data D. Further, the radiotherapy treatment system 100 comprises a total scatter factor unit 130, configured for determining estimated a total scatter factor St using the determined head scatter factor Sh and the determined phantom scatter factor Sp. The head scatter factor unit 110, the phantom scatter factor unit 120 and the total scatter factor unit 130 together is referred to as scatter model.

Figure 5:
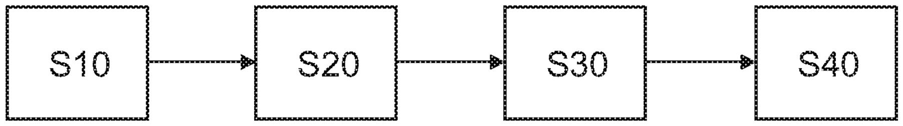
FIG. 5 schematically illustrates a method for estimating a total scatter factor in dose calculation for radiotherapy.

FIG. 5 schematically illustrates a method for estimating a total scatter factor St in dose calculation for radiotherapy, wherein a linear accelerator, LINAC, is used to irradiate a medium. In a first step S10, geometric data D of the LINAC is received, wherein the geometric data D comprises geometric information about a LINAC head of the LINAC, wherein the LINAC head comprises at least one collimating device 10, 20 and at least one irradiation source. In a second step S20, a head scatter factor Sh is determined based on a geometric head model using the received geometric data D, wherein the head scatter factor Sh quantifies a scatter contribution from the LINAC head. In a third step, a phantom scatter factor Sp is determined based on an empiric phantom scatter formula using the received geometric data D, wherein the phantom scatter factor Sp quantifies a scatter contribution from the irradiated medium. In a fourth step, S40 an estimated total scatter factor St is determined using the determined head scatter factor Sh and the determined phantom scatter factor Sp.

The invention claimed is:

1. A computer-implemented method for estimating a total scatter factor in dose calculation for radiotherapy, wherein a linear accelerator (LINAC) is used to irradiate a medium, the method comprising:

receiving geometric data of the LINAC, wherein the geometric data comprises geometric information about a LINAC head of the LINAC, wherein the LINAC head comprises at least one collimating device and at least one irradiation source, wherein the at least one collimating device comprises at least one multi leaf collimator (MLC) defining an MLC plane perpendicular to an irradiation direction of the LINAC, and jaws defining a jaw plane perpendicular to the irradiation direction of the LINAC, wherein the geometric data of the LINAC comprises leaf positions of leaves of the MLC and a jaw position of the jaws;

determining a head scatter factor based on a geometric head model using the received geometric data, wherein the head scatter factor quantifies a scatter contribution from the LINAC head;

determining a phantom scatter factor based on an empiric phantom scatter formula using the received geometric data, wherein the phantom scatter factor quantifies a scatter contribution from the irradiated medium;

determining an estimated total scatter factor using the determined head scatter factor and the determined phantom scatter factor;

determining at least one MLC opening in the MLC using the received leaf positions;

determining, for each MLC opening, a rectangular equivalent field using the received leaf positions;

determining, for each MLC opening, the head scatter factor based on the geometric head model using the determined rectangular equivalent field and the jaw position; and determining, for each MLC opening, the phantom scatter factor based on the empiric phantom scatter formula using the determined rectangular equivalent field and the jaw position.

2. The method of claim 1, wherein determining the rectangular equivalent field comprises:

determining a bounding box around the opening of the MLC plane; and determining the rectangular equivalent field by scaling down the bounding box such that the scaled down bounding box covers an area equal to an area that the MLC opening covers.

3. The method of claim 2, wherein determining the rectangular equivalent field comprises:

determining a radiologic field using the received leaf positions, wherein the radiologic field reflects a geometric design of the leaves of the MLC; and determining the rectangular equivalent field using the radiologic field.

4. The method of claim 1, wherein determining the head scatter factor comprises for each rectangular equivalent field:

shifting the MLC plane so that a center of the rectangular equivalent field is disposed on a central axis of the LINAC along the irradiation direction of the LINAC;

shifting the jaw plane by the same amount as the MLC plane so that a spatial alignment of the jaws to the MLC openings does not change;

determining a detector eye view, being a part of a LINAC source plane that is visible from a detector position, wherein the irradiation source of the LINAC is disposed in the LINAC source plane, wherein the detector position is defined by an intersection of the central axis of the LINAC and a detector plane on which the irradiation of the LINAC is detected; and determining the head scatter factor by determining a total intensity of the irradiation source in the detector's eye view.

5. The method of claim 4, wherein the irradiation source comprises at least one Gaussian source, approximating of the irradiation source.

6. The method of claim 5, wherein the irradiation source comprises a plurality of Gaussian sources at different heights in the LINAC head, approximating of the irradiation source.

7. The method of claim 6, wherein the plurality of Gaussian sources comprises a primary source and at least one secondary source.

8. The method of claim 7, wherein the geometric head model further comprises adjustable fit head parameters and fixed head parameters, depending on a configuration of the LINAC and a measurement setup of the LINAC, the adjustable fit head parameters comprising one or more of: a dimension of the primary source and a dimension and weight relative to the primary source of the at least one secondary source.

9. The method of claim 8, wherein the fixed head parameters comprise one or more of: a distance of the secondary sources from the primary source, a distance of the jaw plane from the primary source, a distance of the MLC plane from the primary source, a source-surface distance, being a distance between the irradiation source and a surface plane to be irradiated by the LINAC, and a measurement depth, being a distance between the surface plane to be irradiated by the LINAC and the detector position.

10. The method of claim 1, wherein the empiric phantom scatter formula comprises adjustable fit phantom parameters and fixed phantom parameters, depending on one or more of: a configuration of the LINAC and a measurement setup of the LINAC.

11. The method of claim 1, wherein the empiric phantom scatter formula comprises adjustable fit phantom parameters and fixed phantom parameters, depending on one or more of: a configuration of the LINAC and a measurement setup of the LINAC, the fixed phantom parameters comprising one or more of: the rectangular equivalent field and a measurement depth.

12. The method of claim 1, wherein the MLC leaf positions comprise two leaf coordinates for each pair of leaves of the MLC.

13. The method of claim 1, wherein the jaw plane comprises four jaws and wherein the jaw position comprises one coordinate for each jaw.

14. The method of claim 1, wherein the at least one MLC opening is smaller than 5 cm in one direction.

15. A method for commissioning a linear accelerator, LINAC, the method comprising:

measuring a total scatter factor of the LINAC by using a measurement setup; and automatically optimizing, using the measured total scatter factor, the geometric head model and the empiric phantom scatter formula according to the method of claim 1.

16. The method of claim 15, further comprising:

determining a deviation between a best-fit result of the estimated total scatter factor and the measured total scatter factor; and providing a warning to a user when the deviation exceeds a threshold.

17. A computer-implemented method for estimating a total scatter factor in dose calculation for radiotherapy, wherein a linear accelerator (LINAC) is used to irradiate a medium, the method comprising:

receiving geometric data of the LINAC, wherein the geometric data comprises geometric information about a LINAC head of the LINAC, wherein the LINAC head comprises at least one collimating device and at least one irradiation source;

determining a head scatter factor based on a geometric head model using the received geometric data, wherein the head scatter factor quantifies a scatter contribution from the LINAC head, wherein the geometric head model further comprises adjustable fit head parameters and fixed head parameters, depending on a configuration of the LINAC and a measurement setup of the LINAC;

determining a phantom scatter factor based on an empiric phantom scatter formula using the received geometric data, wherein the phantom scatter factor quantifies a scatter contribution from the irradiated medium; and determining an estimated total scatter factor using the determined head scatter factor and the determined phantom scatter factor.

18. A non-transitory computer readable medium storing instructions, which when executed by a computer, causes the computer to perform a computer-implemented method for estimating a total scatter factor in dose calculation for radiotherapy, wherein a linear accelerator (LINAC) is used to irradiate a medium, the method comprising:

receiving geometric data of the LINAC, wherein the geometric data comprises geometric information about a LINAC head of the LINAC, wherein the LINAC head comprises at least one collimating device and at least one irradiation source;

determining a head scatter factor based on a geometric head model using the received geometric data, wherein the head scatter factor quantifies a scatter contribution from the LINAC head, wherein the geometric head model further comprises adjustable fit head parameters and fixed head parameters, depending on a configuration of the LINAC and a measurement setup of the LINAC;

determining a phantom scatter factor based on an empiric phantom scatter formula using the received geometric data, wherein the phantom scatter factor quantifies a scatter contribution from the irradiated medium; and determining an estimated total scatter factor using the determined head scatter factor and the determined phantom scatter factor.

19. A non-transitory computer readable medium storing instructions, which when executed by a computer, causes the computer to perform a computer-implemented method for estimating a total scatter factor in dose calculation for radiotherapy, wherein a linear accelerator (LINAC) is used to irradiate a medium, the method comprising:

receiving geometric data of the LINAC, wherein the geometric data comprises geometric information about a LINAC head of the LINAC, wherein the LINAC head comprises at least one collimating device and at least one irradiation source, wherein the at least one collimating device comprises at least one multi leaf collimator (MLC) defining an MLC plane perpendicular to an irradiation direction of the LINAC, and jaws defining a jaw plane perpendicular to the irradiation direction of the LINAC, wherein the geometric data of the LINAC comprises leaf positions of leaves of the MLC and a jaw position of the jaws;

determining a head scatter factor based on a geometric head model using the geometric data, wherein the head scatter factor quantifies a scatter contribution from the LINAC head;

determining a phantom scatter factor based on an empiric phantom scatter formula using the geometric data, wherein the phantom scatter factor quantifies a scatter contribution from the medium;

determining an estimated total scatter factor using the head scatter factor and the phantom scatter factor;

determining at least one MLC opening in the MLC using the leaf positions;

determining, for each MLC opening, a rectangular equivalent field using the leaf positions;

determining, for each MLC opening, the head scatter factor based on the geometric head model using the rectangular equivalent field and the jaw position; and determining, for each MLC opening, the phantom scatter factor based on the empiric phantom scatter formula using the rectangular equivalent field and the jaw position.

* * * * *